US010967195B2

(12) United States Patent
van Rhoon et al.

(10) Patent No.: US 10,967,195 B2
(45) Date of Patent: Apr. 6, 2021

(54) HYPERTHERMIA SYSTEM AND A METHOD FOR GENERATING A FOCUSED THREE-DIMENSIONAL RF FIELD

(75) Inventors: Gerard Cornelis van Rhoon, Rotterdam (NL); Margarethus Marius Paulides, Rotterdam (NL); Jurriaan Fokke Bakker, Rotterdam (NL); Roelf Albert Roskam, Rotterdam (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 1629 days.

(21) Appl. No.: 14/239,658

(22) PCT Filed: Aug. 19, 2011

(86) PCT No.: PCT/NL2011/050569
§ 371 (c)(1),
(2), (4) Date: Jun. 19, 2014

(87) PCT Pub. No.: WO2013/028064
PCT Pub. Date: Feb. 28, 2013

(65) Prior Publication Data
US 2014/0336734 A1    Nov. 13, 2014

(51) Int. Cl.
*A61N 5/00* (2006.01)
*A61N 1/40* (2006.01)
*A61B 17/00* (2006.01)

(52) U.S. Cl.
CPC .............. *A61N 5/00* (2013.01); *A61N 1/403* (2013.01); *A61B 2017/00022* (2013.01)

(58) Field of Classification Search
CPC ........................ A61N 2005/1096; A61N 1/403
See application file for complete search history.

(56) References Cited

U.S. PATENT DOCUMENTS 5,097,844 A * 3/1992 Turner ..................... A61N 5/02
                                                              600/549
5,492,122 A * 2/1996 Button ................... A61N 1/403
                                                              324/315
(Continued)

OTHER PUBLICATIONS

M.M. Paulides, The HYPERcollar: A novel applicator for hyperthermia in the head and neck, Nov. 2007, International Journal of Hyperthermia; 23(7): 567-576.*
(Continued)

*Primary Examiner* — Linda C Dvorak
*Assistant Examiner* — Yasamin Ekrami
(74) *Attorney, Agent, or Firm* — Leydig, Voit & Mayer, Ltd.

(57) ABSTRACT

The invention relates to a hyperthermia system for treating a patient, comprising an RF power unit, one or more RF antenna's connected to the RF power unit for generating a focused three-dimensional RF field, a controller for adjusting the RF power source and/or the one or more RF antenna's for steering the focused three-dimensional RF field; a sensor for sensing a parameter representative of the focused three-dimensional RF field; a communication environment for inputting data from the said sensor and/or additional information provided by the patient, said communication environment being capable of generating trigger signals to the controller for in use steering the focused three-dimensional RF filed in real time. The invention further relates to a method for generation a focused three-dimensional RF field.

13 Claims, 5 Drawing Sheets

(56) References Cited

U.S. PATENT DOCUMENTS

| | | | | |
|---|---|---|---|---|
| 6,330,479 B1* | 12/2001 | Stauffer | .................. | A61N 5/02 |
| | | | | 607/101 |
| 6,494,901 B1* | 12/2002 | Doty | .................... | A61N 5/0614 |
| | | | | 250/504 R |
| 6,575,969 B1* | 6/2003 | Rittman, III | ....... | A61B 18/1482 |
| | | | | 128/898 |
| 7,276,716 B1* | 10/2007 | Munro, III | ........... | A61N 5/1007 |
| | | | | 250/515.1 |
| 2004/0210214 A1* | 10/2004 | Knowlton | .............. | A61B 18/14 |
| | | | | 606/41 |
| 2010/0217253 A1* | 8/2010 | Mehta | ................ | A61B 18/1477 |
| | | | | 606/33 |
| 2012/0330284 A1* | 12/2012 | Hyde | .................... | A61B 18/12 |
| | | | | 606/1 |

OTHER PUBLICATIONS

"International Application No. PCT/NL2011/050569 International Search Report", (dated Apr. 25, 2012), 3 pgs.

"International Application No. PCT/NL2011/050569 International Written Opinion", (dated Apr. 25, 2012), 6 pgs.

* cited by examiner

PRIOR ART

HYPERTHERMIA SYSTEM AND A METHOD FOR GENERATING A FOCUSED THREE-DIMENSIONAL RF FIELD

PRIORITY APPLICATION

This application is a U.S. National Stage Filing under 35 U.S.C. § 371 from International Application Number PCT/NL2011/050569, filed on 19 Aug. 2011, and Published as WO/2013/028064, on 28 Feb. 2013, which application and publication are hereby incorporated herein by reference in their entirety.

FIELD OF THE INVENTION

The invention relates to a hyperthermia system.
The invention further relates to a method of generating a focused three-dimensional RF field.

BACKGROUND OF THE INVENTION

An embodiment of a hyperthermia system is known from U.S. Pat. No. 5,097,844. The known system is arranged to generate a three-dimensional focusing hyperthermia. The known system comprises a controller connected to a signal modifier capable of modifying a phase and a power amplitude of a multiple channel RF power system. A switching assembly is used to connect to a suitable antenna group forming the applicator of the known hyperthermia apparatus.

In order to determine a temperature at or near a target area of the focused three-dimensional RF power system, the known hyperthermia apparatus comprises a non-invasive thermometry sensor. The thermometry sensor is connected to the controller via a temperature monitor.

Hyperthermia systems known in the art usually operate using a treatment planning system which is configured to simulate the envisaged treatment and to calculate suitable settings for the RF antenna or RF antenna's for implementing the treatment. Should, however, in use, the determined temperature in the target region substantially deviate from a planned temperature, the controller may be activated automatically or manually for steering the RF antenna or antenna's for correcting the temperature profile or position of the hot region.

It is a disadvantage of the known hyperthermia system that limited control of the correspondence between the planned treatment and the actual treatment is available.

SUMMARY OF THE INVENTION

It is an object of the invention to provide a hyperthermia apparatus wherein the control of deposition of the RF energy is improved. In particular, it is an object of the invention to provide a hyperthermia apparatus wherein a substantially continuous control of the RF energy is enabled.

To this end the hyperthermia apparatus according to the invention comprises:
an RF power unit;
one or more RF antenna's connected to the RF power unit for generating a focused three-dimensional RF field;
a controller for adjusting the RF power source and/or the one or more RF antenna's for steering the focused three-dimensional RF field;
a sensor for sensing a parameter representative of the focused three-dimensional RF field;
a communication environment for inputting data from the said sensor and/or additional information provided by the patient, said communication environment being capable of generating trigger signals to the controller for in use steering the focused three-dimensional RF filed in real time.

It is found that current hyperthermia systems are not suited for hyperthermia application on several parts of the body, such as head and neck region. In addition, the known systems do not take into account patient tolerability of the hyperthermia treatment so that a feedback from the system is limited to a sensor feedback regarding actual temperature in or near the target region. The feedback may, for example, comprise phase and amplitude data of a measured E-field. Provided that the hyperthermia delivery system is calibrated, the E-field data are directly related to the temperature.

Preferably, the controller is arranged for enabling a substantially continuous adjusting the RF power source and/or the one or more RF antenna's for steering the focused three-dimensional RF field. However, it will be appreciated that the controller may be adapted to cyclically adjust the RF power source and/or the one or more RF antenna's or to carry such adjustment in accordance with a pre-planned protocol. It will be further appreciated that a sensor may comprise a sensor system. The sensor may be adapted to receive suitable data inside or outside the patient. For example, for an E-field sensor collecting data outside the patient may be advantageous.

In accordance to the invention an integrated system is provided enabling to incorporate sensor data and/or information supplied by the patient into the system controls for steering a position and/or a temperature of the focused three-dimensional RF field. It will be appreciated that the hyperthermia system according to the invention may be adapted to modify a portion of a target region corresponding to the elevated temperatures.

In the hyperthermia system according to the invention a communication environment is provided which is capable of inputting patient information into a control system. For example, the communication environment may be embodied as a speech recognition platform for interpreting the patient's complaints or suggestions into a set of control signals enabling steering of the focused three-dimensional RF field. In another embodiment, the communication environment may be embodied as an anatomical model having characteristic points or areas, such as target region and critical organs. The anatomical model may be provided with textual comments which will be used for generating suitable control signals for steering the focused three-dimensional RF field. Still alternatively, the communication environment may be embodied as a look-up table to be filled in by an operator of the hyperthermia system based on the patient's complaints or suggestions. The look-up table may then be automatically translated into a set of trigger signals to modify the focused three-dimensional RF field in real-time.

In an embodiment of the hyperthermia system the RF antenna's are arranged on an applicator comprising a water bolus, the water bolus being shaped to allow breathing and verbal communication by the patient.

It is found that challenges of the head and neck treatment may be met provided a suitably shaped applicator is used. A cranial or head and neck applicator may be used. In accordance with the present aspect of the invention, the applicator is shaped to allow breathing and verbal communication. In this way the patient's input information may be suitably provided for use in the hyperthermia system.

In a further embodiment of the hyperthermia system according to the invention the applicator is substantially cylindrically shaped having two displaceable portions, the bolus comprises two isolated parts each provided on a corresponding displaceable portion of the cranial applicator.

It is found to be particularly advantageous to provide an applicator, which, being substantially cylindrically shaped, may be open on demand. In order not to deform the bolus extensively, the bolus is divided into two isolated parts, which are integrated with the corresponding displaceable portion of the applicator. Such configuration has an additional effect—when the parts of the applicator are joined together about a patient, by virtue of surface tension of the bolus parts, a cavity may be created. When the parts are symmetrical with respect to the longitudinal axis of the patient, the cavity formed in the bolus may advantageously correspond to the nose area of the patient thereby simplifying breathing. However, it will be appreciated that the applicator according to the invention does not extend in a longitudinal direction further than the patient's mouth leaving the possibility for him to express himself verbally.

In a still further embodiment of the hyperthermia system according to the invention the two displaceable portions are pivotable with respect to each other.

It will be appreciated that the two parts may be connected though a pivot, or, alternatively, the parts may be connected to a base so that each displaceable portion is individually pivotable with respect to the base. In this arrangement two pivots may be necessary, each for one displaceable portion.

In a still further embodiment of the hyperthermia system according to the invention a pre-shaped insert is provided inside the applicator for shaping and/or supporting the water bolus.

It will be appreciated that the pre-shaped insert is manufactured in accordance with a desired substantially permanent shape of the bolus at least during the treatment for matching a patient's landscape. It is found that due to the existent landscape of the human head and neck region, it may be advantageous to shape the bolus and at least the inner side of the applicator substantially conforming to the outer shape of, for example, the human head and neck. In a particular embodiment at least a portion of the water bolus arranged to contact the patient is pre-shaped. It will be appreciated that different sizes of the applicator may be provided for matching an infant anatomy on one hand, and an adult anatomy, on the other hand. Preferably, the insert is manufactured from foam. More in particular, the water bolus may be replaceable so that the applicator may be used with different bolus for different anatomies. Alternatively or additionally, the bolus may be shaped to accommodate a specific need. For example, the bolus may be provided with a cavity for allowing breathing. More details on the applicator will be given with respect to figure description.

The method of generating a focused three-dimensional RF field in a patient, according to an aspect of the invention comprises the steps of:
 generating a focused three-dimensional RF field using one or more RF antenna's;
 enabling steering the focused three-dimensional RF field;
 using a parameter representative of the focused three-dimensional RF field provided by a sensor and/or additional information provided by the patient, for in use steering the focused three-dimensional RF filed in real time.

It will be appreciated that the method according to the invention may advantageously comprise the step of calibrating the hyperthermia delivery system beforehand or in use.

It will be appreciated that the said focused three-dimensional RF field may be not therapeutic. Alternatively, the said focused three-dimensional RF field may be planned to have a therapeutic effect.

These and other aspects of the invention will be discussed in more detail with reference to figures wherein like reference numerals refer to like elements. It will be appreciated that the figures are presented for illustrative purposes and may not be used for limiting the scope of the appended claims.

DETAILED DESCRIPTION

Figure 1:
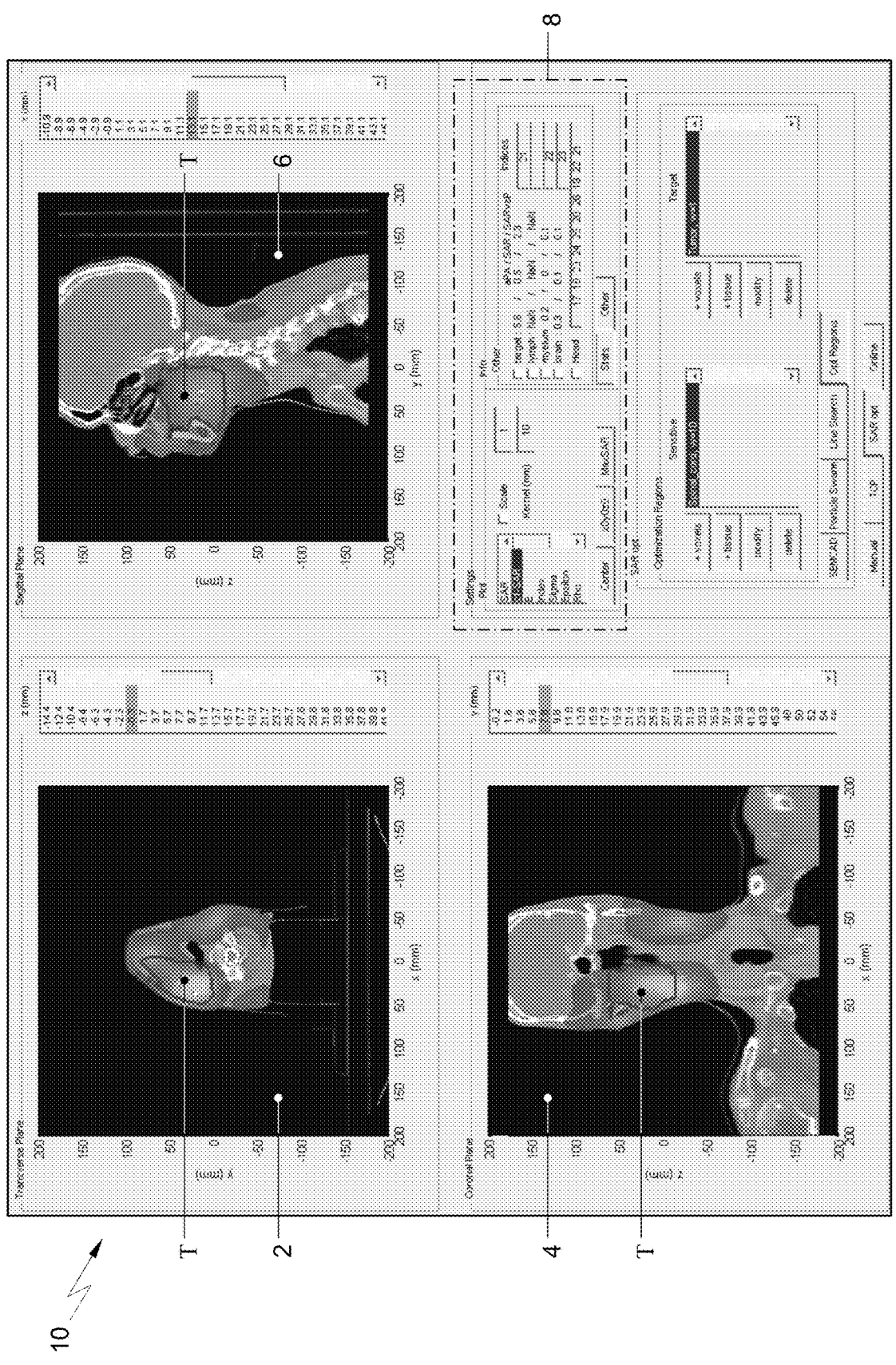
FIG. 1 presents in a schematic way an embodiment of a hyperthermia treatment plan.

FIG. 1 presents in a schematic way an embodiment of a hyperthermia treatment plan for the head and neck region. A suitable automatic treatment plan system may be used for calculating temperature profiles in a patient based on the diagnostic data of the patient. Usually the treatment planning system makes use of the pre-stored electromagnetic field profiles as may be generated by each of the antenna's forming part of the hyperthermia system. By varying respective weights and phases of the antenna's the treatment planning system arrives at a resulting temperature or temperature-related profile which may be substantially conformal to the target region T. In FIG. 1 an exemplary embodiment of a resulting temperature profile is presented for a cross-sectional image 2, a saggital image 6 and a coronal image 4. The treatment planning system output data 8 which are representative of the resulting temperature profile and may be used for steering the hyperthermia system in use.

Figure 2:
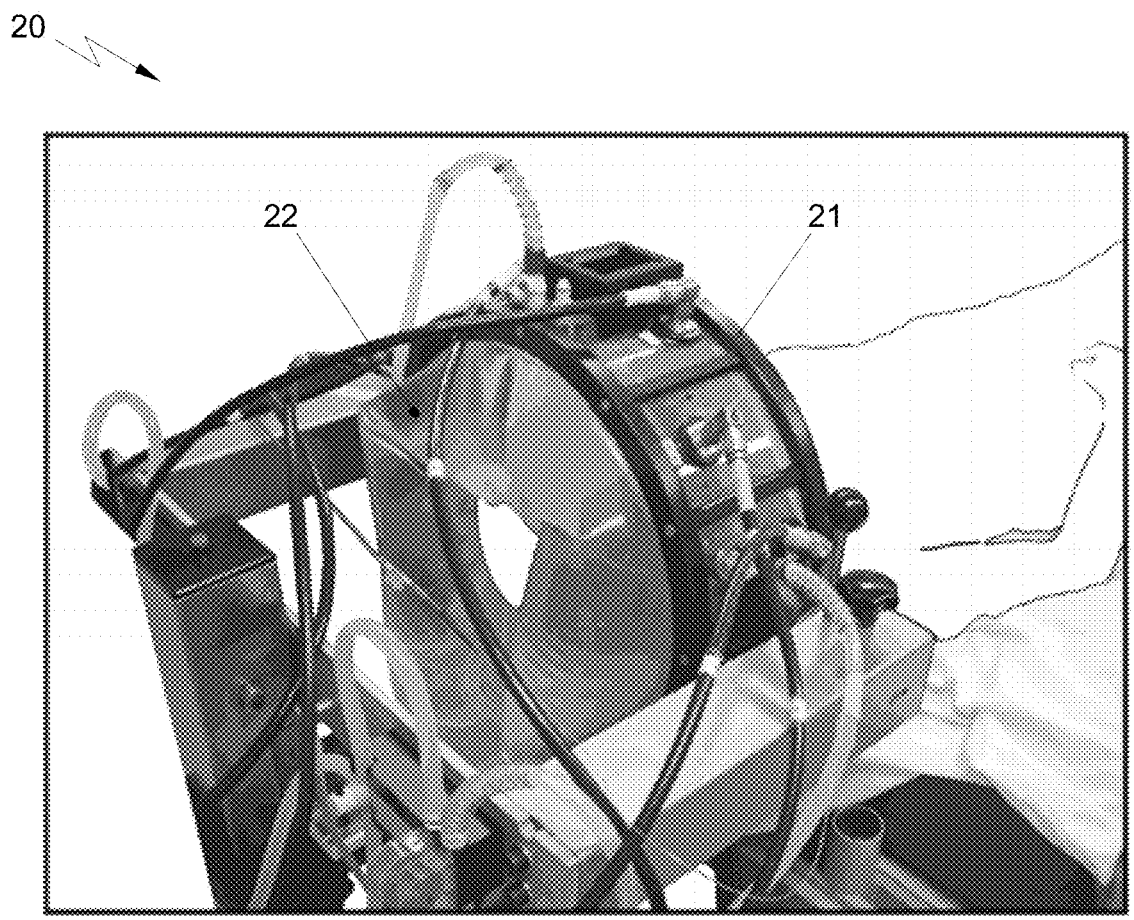
FIG. 2 presents in a schematic way an embodiment of a hyperthermia system known from the prior art.

FIG. 2 presents in a schematic way an embodiment of a hyperthermia system known from the prior art. The prior art hyperthermia system 20 comprises a solid ring 21 accommodating a series of RF antenna's, a water bolus 22. Suitable cabling is provided for feeding the RF antenna's. The water bolus 22 is connected to an external pump for enabling circulation for increasing cooling capacity of the bolus. The known hyperthermia system has a disadvantage that the patient's comfort during the treatment is limited. This is explained by the fact that the patient's head is almost fully covered by the water bolus 22 which may even hamper normal breathing. The prior art system 20 does not allow the patient to verbally communicate during the treatment because the mouth area is usually covered with the bolus.

Figure 3:
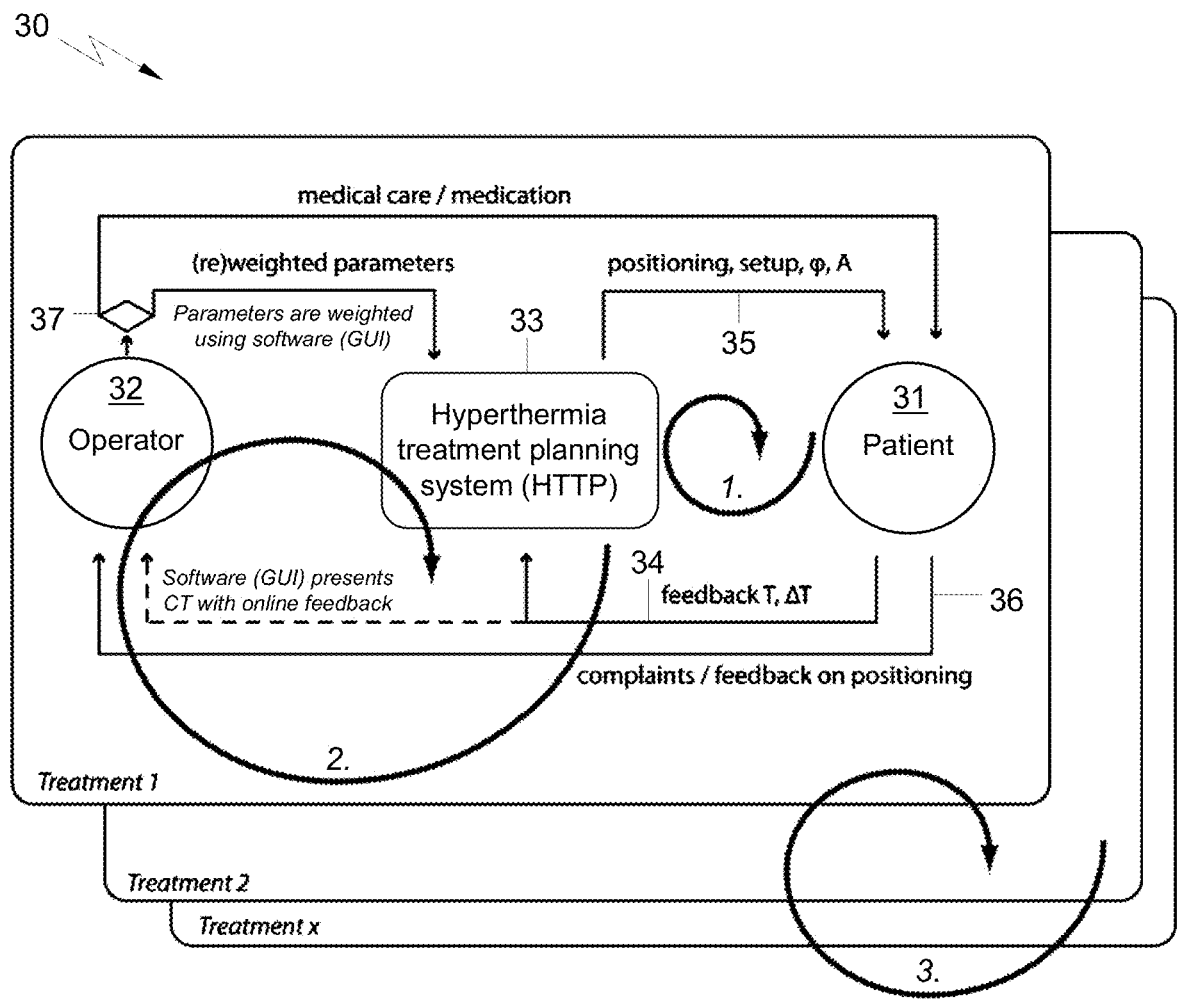
FIG. 3 presents in a schematic way an embodiment of a block-scheme of a hyperthermia system according to an aspect of the invention.

FIG. 3 presents in a schematic way an embodiment of a block-scheme of a hyperthermia system according to an aspect of the invention. In accordance with an aspect of the invention, the patient 31 may be monitored by a suitable sensor, such as a temperature sensor, or an E-field sensor, or an MR-system for monitoring the appropriate parameter during treatment in or at the target region or other parts of the patient or applicator system. It will be appreciated that the appropriate parameter may be the temperature or may relate to a physical value representative of the temperature. Such examples are not limiting. Data 34 collected by a suitable sensor are fed back to the hyperthermia planning system 33 which may adjust the settings of the RF antenna's of the hyperthermia apparatus in real time. For example, suitable trigger signals 35 may be generated for altering a position of the active elements of the RF antenna's, their respective phases, power amplitude and so on.

Next to the data communication loop 34, the hyperthermia system according to the invention comprises a patient communication loop 36, i.e. a communication environment enabling the patient to communicate his complains and suggestions. For example, as a speech recognition platform may be provided to cooperate with the hyperthermia planning system 33 for interpreting the patient's complaints or suggestions into a set of control signals 37 enabling steering of the focused three-dimensional RF field. For example, should the patient experience thermal discomfort in a certain area, the RF antenna's may be adapted to reduce the net temperature only in that particular region. It will be appreciated that the control signals 37 may be generated using a suitable optimization algorithm which optimizes the treatment plan with regard to the new constrains.

In another embodiment, the communication environment may be embodied as an anatomical model having characteristic points or areas, such as target region and critical organs. The anatomical model may be provided with textual comments which will be used for generating suitable control signals. For example, the patient may indicate which organs or areas are overheated and the operator 32 of the hyperthermia system may label or mark these area's accordingly. The controls of the hyperthermia system 33 will recognize such input and convert it into a series of trigger signals 37 for steering the RF antenna's thereby suitably modifying the net temperature or temperature-related profile.

Still alternatively, the communication environment may be embodied as a look-up table to be filled in by an operator 32 of the hyperthermia system based on the patient's complaints or suggestions. The look-up table may then be automatically translated into a set of trigger signals 37 together with the hyperthermia planning system 33 to modify the focused three-dimensional RF field in real-time.

In all of the scenarios the operator 32 is also capable to overrule the hyperthermia planning system 33 based on the data 34 provided by the sensor. This may be executed using a suitable user interface whereon actual temperature profile is superposed on the patient diagnostic data, such as CT or MRI scans. The operator may also request support from a coaching system (not shown) regarding suitable patient handling should the patient discomfort be excessive.

Figure 4:
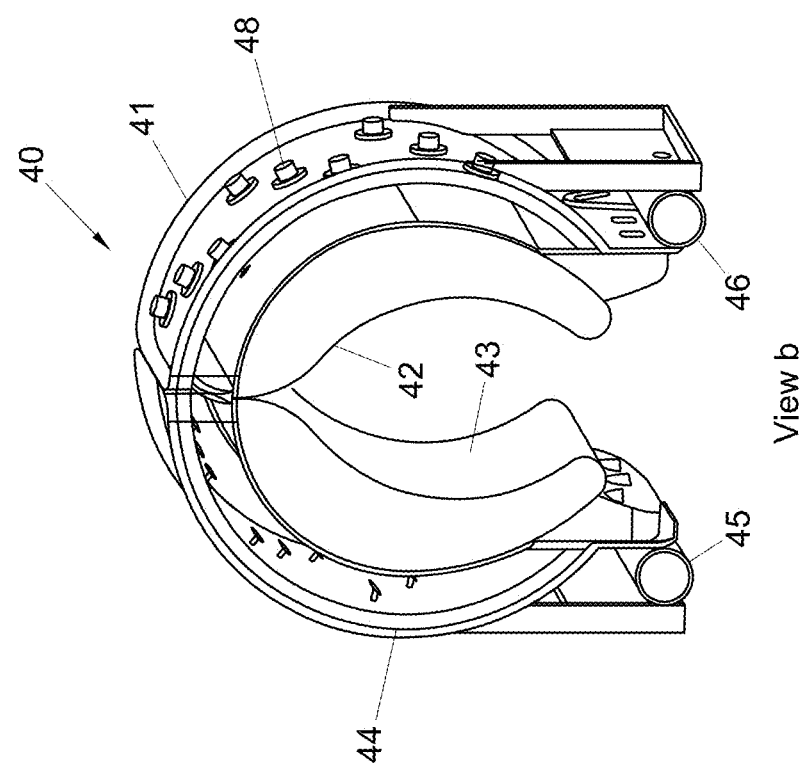
FIG. 4 presents in a schematic way an embodiment of an applicator in accordance with an aspect of the invention.
Figure 4:
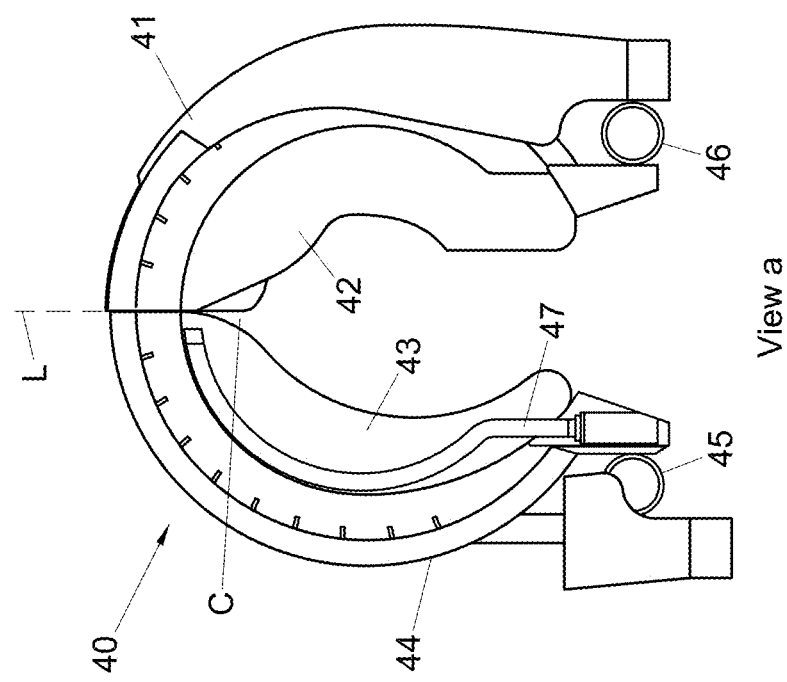

FIG. 4 presents in a schematic way an embodiment of an applicator in accordance with an aspect of the invention. The applicator 40 comprises two displaceable parts 41, 44 which are pivotably arranged with respect to the pivots 45, 46. Accordingly, the displaceable parts 41, 42 may be turned open with respect to the longitudinal axis L. It will be appreciated that usually the axis L is selected to substantially coincide with the longitudinal axis of the patient so that a cavity C coincides with the nose area, see view "a". However, it may be envisaged that the displaceable parts 41, 44 are opened in a different way than indicated.

The applicator 40 further comprises two separated parts of the water bolus, each part 42, 43 being affixed to a corresponding portion of the cranial applicator. Suitable tubing 47 (one is shown) may be provided externally to arrange the bolus parts to an external fluid system for circulating water in the bolus. This may be useful for increasing the cooling capacity of the bolus.

View "b" presents schematically a three-dimensional representation of the applicator discussed with reverence to view "a". In this view it is seen that the cabling connectors 48 are provided to connect an external power supply to the RF antenna's provided in the applicator. In this figure the RF antenna's are not depicted for clarity.

It will be appreciated that although in FIG. 4 a substantially cylindrical applicator is depicted wherein each displaceable portion of the applicator is pivotable about its own pivot, other configurations are possible. For example, it is possible to provide the applicator wherein the displaceable portions 41, 44 are joined together at the dorsal area and are pivotable about a common pivot. Also, it is possible that the applicator is obliquely mounted with respect to the mounting base or patient table (not shown). This has an advantage for treatment of neck regions so that the oblique inclination of the applicator avoids the chin area of the patient. The described applicator may relate to a cranial applicator or a head and neck applicator.

Figure 5:
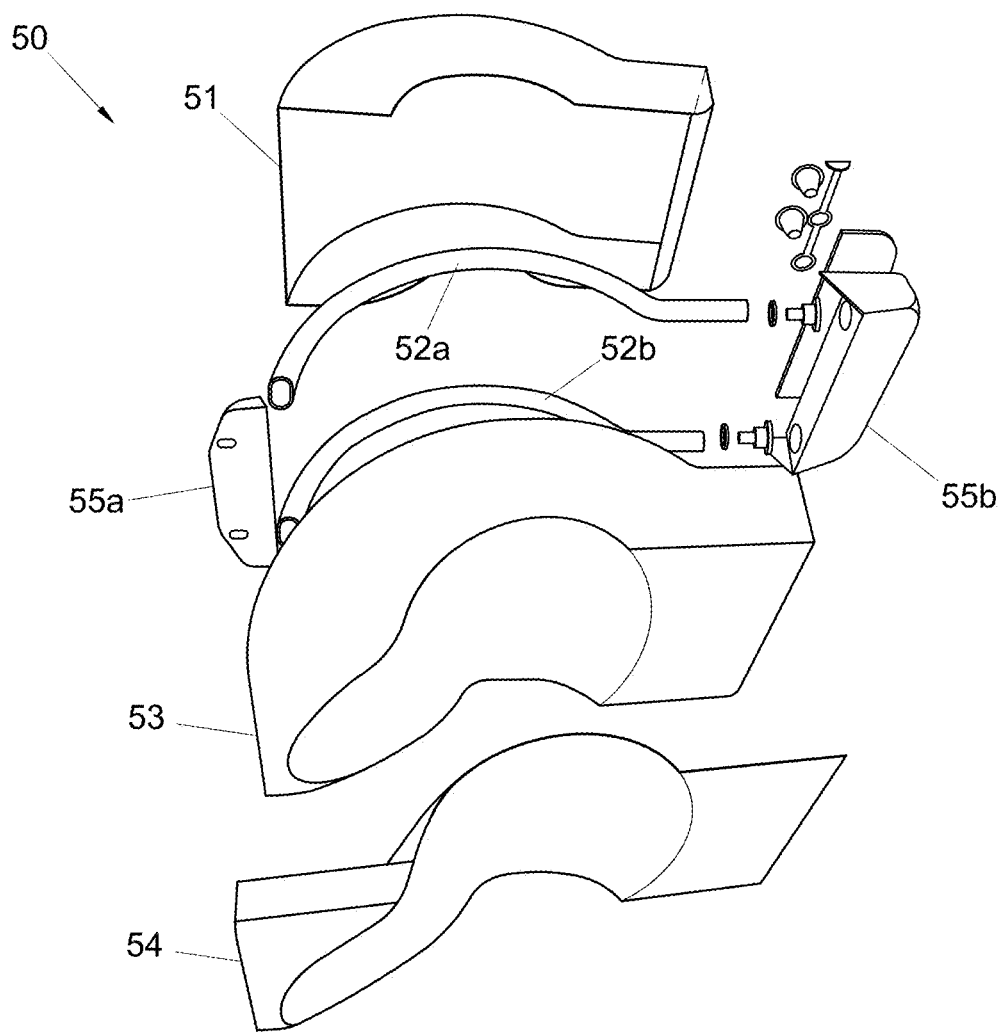
FIG. 5 presents in a schematic way a further embodiment of the applicator, shown in FIG. 4.

FIG. 5 presents in a schematic way a further embodiment of the applicator, shown in FIG. 4. In this figure a sandwiched structure of one displaceable portion 50 of the applicator is depicted. In accordance with the invention, an external housing 54 is provided in a suitable shape. It will be appreciated that a plurality of shapes are possible meeting geometry of the patients from different groups and different treatment locations. For example, for a cranial application, the external housing 54 may be shaped to have a shell-like structure geometrically conforming to a shape of a human head.

The external housing 54 is used for supporting a suitably shaped insert 53, which may be manufactured from foam. The insert is used to pre-shape the water bolus 51, which may be fed using the circulation tubes 52a, 52b. The circulation tubes may be mounted inside the applicator using suitable mounting means 53a, 53b. It is found that it is particularly advantageous to arrange the water bolus with a substantially rigid surface which is arranged to contact a patient. Because patient's anatomies are different it is further advantageous to replaceably mount the bolus inside the applicator.

It will be further appreciated that an aspect of the invention relates to the applicator as is described with reference to FIGS. 4 and 5, which may be used independent of the hyperthermia system as is set forth with reference to FIG. 3.

It will be further appreciated that while specific embodiments of the invention have been described above, the invention may be practiced otherwise than as described.

The invention claimed is:

1. A hyperthermia system for treating a patient, comprising:
   an RF power unit;
   one or more RF antennas connected to the RF power unit for generating a focused three-dimensional RF field;
   a treatment planning system comprising a controller for adjusting, in real time during the treating the patient, either or both an output of the RF power source or the one or more RF antennas, the adjusting causing a steering of the focused three-dimensional RF field to obtain a desired temperature related profile;

a sensor for sensing a parameter representative of the focused three-dimensional RF field generated by the antennas;

a communication environment configured to carry out a real time feedback loop-based control method comprising:

receiving a sensor data from the sensor and a patient feedback information provided by the patient;

generating in real time, in response to the sensor data and the patient feedback information, trigger signals to the controller for use in steering the focused three-dimensional RF field to adjust the temperature in a region of discomfort within the patient;

superposing a real-time temperature profile on patient diagnostic data using an anatomical model including characteristic points or areas; and filling a look-up table of the hyperthermia system with a feedback content, based on the patient feedback information, in respect to the characteristic points or areas, wherein the feedback content is translated, in real-time, into the trigger signals.

2. The system according to claim 1, wherein the one or more RF antennas are arranged on an applicator, wherein the applicator comprises a bolus, and wherein the bolus is shaped to allow breathing and verbal communication by the patient.

3. The system according to claim 2, wherein the applicator is substantially cylindrically shaped having two or more displaceable portions, wherein the bolus comprises two or more isolated parts, and wherein each of the two or more isolated parts is provided on a corresponding one of the two or more displaceable portions.

4. The system according to claim 3, wherein the two or more displaceable portions are pivotable with respect to each other.

5. The system according to claim 3, wherein the two or more displaceable portions are mounted on a base, each displaceable portion being individually pivotable with respect to the base.

6. The system according to claim 2, wherein the bolus is connected to a liquid circulation system.

7. The system according to claim 2, wherein a pre-shaped insert is provided inside the applicator for shaping and/or supporting the bolus.

8. The system according to claim 7, wherein the pre-shaped insert is manufactured from foam.

9. The system according to claim 2, wherein a surface of the bolus facing the patient is pre-shaped to match the patient surface.

10. The system according to claim 2, wherein the bolus is replaceably attached to the applicator.

11. The system according to claim 3, wherein each one of the two or more displaceable portions are independently displaceable with respect to other ones of the two or more displaceable portions.

12. The system according to claim 3, wherein each one of the two or more displaceable portions are mounted on a base, and wherein each one of two or more displaceable portions is independently displaceable with respect to the base.

13. The system according to claim 2, wherein the bolus comprises two or more isolated parts configured to include connection to an external fluid circulation system that facilitates modifying cooling capacities of the two or more isolated parts by circulating liquid in the two or more isolated parts of the bolus.

* * * * *